(12) United States Patent
Hopper

(10) Patent No.: US 8,795,639 B2
(45) Date of Patent: Aug. 5, 2014

(54) INGESTIBLE ORAL CARE COMPOSITION AND METHOD THEREFOR

(75) Inventor: Barry L. Hopper, Bristol, TN (US)

(73) Assignee: Barry L. Hopper, Bristol, TN (US)

( * ) Notice: Subject to any disclaimer, the term of this patent is extended or adjusted under 35 U.S.C. 154(b) by 0 days.

(21) Appl. No.: 13/492,954

(22) Filed: Jun. 11, 2012

(65) Prior Publication Data

US 2012/0315077 A1    Dec. 13, 2012

Related U.S. Application Data

(60) Provisional application No. 61/495,084, filed on Jun. 9, 2011.

(51) Int. Cl.
*A61Q 11/00* (2006.01)
*A61K 9/00* (2006.01)

(52) U.S. Cl.
USPC ............................................. 424/49; 424/400

(58) Field of Classification Search
CPC ...... A61Q 11/00; A61K 2300/00; A61K 8/19
USPC ..................................................... 424/49, 400
See application file for complete search history.

(56) References Cited

U.S. PATENT DOCUMENTS

| | | | |
|---|---|---|---|
| D440,049 S * | 4/2001 | De Mond et al. | D4/108 |
| 2003/0003059 A1 * | 1/2003 | Dana | 424/49 |
| 2004/0101494 A1 * | 5/2004 | Scott et al. | 424/49 |
| 2005/0147458 A1 * | 7/2005 | Hohlbein | 401/132 |

* cited by examiner

*Primary Examiner* — Lezah W Roberts
*Assistant Examiner* — Tracy Liu
(74) *Attorney, Agent, or Firm* — Carlson, Gaskey & Olds, P.C.

(57) ABSTRACT

An ingestible oral care product includes a composition with xylitol, glycerin, carboxymethylcellulose, sodium bicarbonate and at least one flavoring agent.

8 Claims, 1 Drawing Sheet

FORM AN INGESTIBLE ORAL CARE COMPOSITION INCLUDING XYLITOL, GLYSERIN, CARBOXYMETHYLCELLULOSE, SODIUM BICARBONATE AND AT LEAST ONE FLAVORING AGENT

INGESTIBLE ORAL CARE COMPOSITION AND METHOD THEREFOR

REFERENCE TO RELATED APPLICATION

This application claims priority to U.S. Provisional Application No. 61/495,084, filed on Jun. 9, 2011 and is hereby incorporated in its entirety.

BACKGROUND

This disclosure relates to an ingestible composition.

Toothpaste is known and used to help clean and maintain the health of teeth. The toothpaste promotes oral hygiene and serves as an aid in removing plaque and food from the teeth. Toothpaste may also serve other purposes, such as to suppress halitosis or deliver ingredients that prevent tooth and gum disease. However, many toothpastes or other oral care products contain ingredients that, if ingested, upset the gastric tract. Therefore, most toothpaste compositions are not considered to be ingestible. As a result, oral hygiene has become limited to certain environments, such as in the home.

There are also ingestible forms of toothpaste that may be less irritating to the gastric tract. Even so, these ingestible toothpastes or other oral care products still include small amounts of ingredients that can upset the gastric tract. Other so-called ingestible toothpastes are stripped of active cleaning or hygiene ingredients and therefore are mostly ineffective for maintaining oral hygiene.

SUMMARY

An ingestible oral care product according to an exemplary aspect of the present disclosure includes a composition with xylitol, glycerin, carboxymethylcellulose, sodium bicarbonate and at least one flavoring agent.

A method for making an ingestible oral care product according to an exemplary aspect of the present disclosure includes forming an ingestible oral care composition including xylitol, glycerin, carboxymethylcellulose, sodium bicarbonate and at least one flavoring agent.

A disposable toothbrush according to an exemplary aspect of the present disclosure includes an ingestible toothpaste with a composition including xylitol, glycerin, carboxymethylcellulose, sodium bicarbonate and at least one flavoring agent

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figures 1, 2:
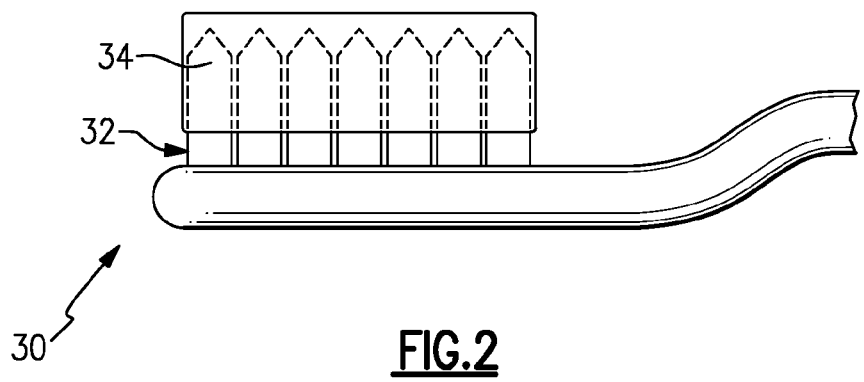
FIG. 1 shows an example method for making an ingestible oral care product.
FIG. 2 shows a disposable toothbrush including an ingestible toothpaste with a composition disclosed herein.

This disclosure relates to an ingestible oral care composition, products that utilize the ingestible oral care composition and methods for making the ingestible oral care composition.

In general, oral care products, such as toothpaste, are used to promote oral hygiene and aid in the removal of plaque and food from teeth. Of course, depending upon the composition, the oral care product may also serve other functions. Whatever the purpose of the user, there is a need to maintain oral hygiene in almost in any environment. In these regards, the ingestible oral care composition disclosed herein provides the opportunity to maintain oral hygiene in any number of different environments, including away from home.

Many oral care products include ingredients that are not considered to be ingestible. For instance, such oral care products include fluoride, which if ingested, can cause gastric irritation, or worse. Oral care products may also include other ingredients that are not considered to be ingestible and cause gastric irritation or worse. In this regard, the ingestible oral care composition disclosed herein contains a limited number of ingredients, and the included ingredients are ingestible, to avoid gastric irritation.

The following examples are of a toothpaste that includes the disclosed oral care composition. It is to be understood that the examples disclosed herein are not limited to toothpastes and that the ingestible oral care composition may alternatively be used in candies, gum lozenges, mints, mouth wash, or other dental/oral care products. The exemplary ingestible toothpaste composition includes xylitol, glycerin, carboxymethylcellulose, sodium bicarbonate, and one or more flavoring agents. For instance, the flavoring agents include peppermint, spearmint, wintergreen or other desirable flavors. In a further embodiment, the ingestible toothpaste contains only these ingredients, to the exclusion of all other ingredients, including water.

In a further example of the disclosed composition, the ingestible toothpaste includes, for better effectiveness, equal amounts by weight of the xylitol and the glycerin. In a further example, the ingestible toothpaste composition also includes less carboxymethylcellulose by weight than sodium bicarbonate. In yet a further example, the ingestible toothpaste composition also includes less of the flavoring agent or agents by weight than sodium bicarbonate. Also, as is evident by the disclosed compositions, the ingestible toothpaste is a non-aqueous composition.

In one example, the ingestible toothpaste includes 40-49 wt. % of the xylitol, 40-49 wt. % of the glycerin, a non-zero amount of less than 1 wt. % of the carboxymethylcellulose, a non-zero amount of less than 5 wt. % of the sodium bicarbonate, and a non-zero amount of less than 2 wt. % of the flavoring agents. For instance, the ingestible toothpaste includes only these ingredients.

In a further example composition, the ingestible toothpaste composition consists of 47-49 wt. % xylitol, 47-49 wt. % glycerin, a nonzero amount less than 0.5 wt. % carboxymethylcellulose, a nonzero mount less than 4 wt. % sodium bicarbonate and a nonzero amount less than 0.5 wt. % of one or more flavoring agents.

In another example, the ingestible toothpaste composition consists of approximately 48.1 wt. % xylitol, approximately 48.1 wt. % glycerin, approximately 0.19 wt. % carboxymethylcellulose, approximately 3.2 wt. % sodium bicarbonate and approximately 0.32 wt. % of one or more flavoring agents. The term "approximately" means +/−0.1 wt. % of the given value. Also in this example, the amounts of xylitol and glycerin are equal, there is less carboxymethylcellulose than sodium bicarbonate and there is less flavoring agent than sodium bicarbonate. In a further example, the glycerin has a 99.5% purity or better.

Depending on the intended end use, the given ingredients of the disclosed ingestible toothpaste are combined using a method 20 as shown in FIG. 1 such that the resulting toothpaste has a desirable consistency. The method 20 therefore also embodies or incorporates the compositions described herein. For instance, the steps of the method produce the toothpaste with the consistency of a paste rather than a product that is too liquid or too solid.

The method 20 includes forming the ingestible oral care composition disclosed herein. In one example, the carboxymethylcellulose is combined with dry xylitol before any heating and is dispersed through the dry xylitol. The amounts of carboxymethylcellulose and xylitol are selected based on the desired end composition of the toothpaste, as described herein. The mixture or combination is then heated above the 199° F. melting point of the dry xylitol to about 240° F. until the xylitol is totally or substantially clear. The mixture is slowly heated to avoid overheating above 240° F.

The glycerin is then separately heated to 100° F. The sodium bicarbonate is then combined with the warm glycerin, stirred and dissolved. The one or more flavoring agents are combined into the mixture of the glycerin and sodium bicarbonate. The heated mixture of carboxymethylcellulose and xylitol is then combined with the glycerin mixture and stirred. The amounts of glycerin, sodium bicarbonate and one or more flavoring agents are selected based on the desired end composition of the toothpaste, as described herein. The mixture or combination of all of the ingredients is stirred and then placed in a cooling bath with continued stirring until the mixture has an opaque appearance, which occurs at about 60° F. The method is then complete and the cooling can be ceased.

The given heating/cooling steps and the shear forces that used in mixing influence the consistency of the end product. In one example, the mixing is conducted at a speed of at least 2500 to 3000 revolutions per minute as the mixture cools to 90° F. For instance, the disclosed example method forms the product as a paste that then turns to a solid, rather than a semi-solid. However, the specific temperatures of heating/cooling and the mixing speed can be varied to allow the material to turn semi-solid, depending upon the end use of the toothpaste. In one example, the consistency is varied by changing the heating time and the heating temperature of the mixture of xylitol and carboxymethylcellulose.

For example, a semi-solid consistency is desired for dispensing the toothpaste into an appropriate container or tube, and a solid consistency is desired for dispensing the toothpaste in a hardened state, such as onto a disposable tooth brush that can be later packaged and distributed. For instance, FIG. 2 shows a disposable (i.e., one-time use) tooth brush 30 having bristles 32 and a pre-dispensed toothpaste 34 on the bristles 32 (as opposed to toothpaste that a user dispenses at the time of use) can be provided to children in schools to brush their teeth after lunch and then dispose of the toothbrush, although the disclosed toothpaste is not limited to disposable toothbrush products.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. An ingestible oral care product consisting of:
a composition consisting of xylitol, glycerin, carboxymethylcellulose, sodium bicarbonate and at least one flavoring agent, wherein the composition consists of, by weight, 40-49% of the xylitol, 40-49% of the glycerin, a non-zero amount of less than 1% of the carboxymethylcellulose, a non-zero amount of less than 5% of the sodium bicarbonate and a non-zero amount of less than 2% of the at least one flavoring agent.

2. The product as recited in claim 1, wherein the composition includes equal amounts by weight of the xylitol and the glycerin.

3. The product as recited in claim 1, wherein the composition includes less of the carboxymethylcellulose than the sodium bicarbonate.

4. The product as recited in claim 1, wherein the composition includes less of the flavoring agent than the sodium bicarbonate.

5. The product as recited in claim 1, wherein the composition is non-aqueous.

6. An ingestible oral care product consisting of:
a composition consisting of xylitol, glycerin, carboxymethylcellulose, sodium bicarbonate and at least one flavoring agent, wherein the composition consists of, by weight, 47-49% of the xylitol, 47-49% of the glycerin, a non-zero amount of less than 0.5% of the carboxymethylcellulose, a non-zero amount of less than 4% of the sodium bicarbonate and a non-zero amount of less than 0.5% of the at least one flavoring agent.

7. An ingestible oral care product consisting of:
a composition consisting of xylitol, glycerin, carboxymethylcellulose, sodium bicarbonate and at least one flavoring agent, wherein the composition consists of, by weight, approximately 48.1% of the xylitol, approximately 48.1% of the glycerin, approximately 0.19% of the carboxymethylcellulose, approximately 3.2% of the sodium bicarbonate and approximately 0.32% of the at least one flavoring agent.

8. A disposable toothbrush including:
an ingestible toothpaste consisting of a composition consisting of xylitol, glycerin, carboxymethylcellulose, sodium bicarbonate and at least one flavoring agent, wherein the composition consists of, by weight, 40-49% of the xylitol, 40-49% of the glycerin, a non-zero amount of less than 1% of the carboxymethylcellulose, a non-zero amount of less than 5% of the sodium bicarbonate and a non-zero amount of less than 2% of the at least one flavoring agent.

* * * * *